United States Patent [19]

Kumman et al.

[11] Patent Number: 4,592,766
[45] Date of Patent: Jun. 3, 1986

[54] PARALLEL STREAM HEAT EXCHANGE FOR SEPARATION OF ETHANE AND HIGHER HYDROCARBONS FROM A NATURAL OR REFINERY GAS

[75] Inventors: Paul Kumman, Munich; Gerhard Ranke, Pocking, both of Fed. Rep. of Germany

[73] Assignee: Linde Aktiengesellschaft, Wiesbaden, Fed. Rep. of Germany

[21] Appl. No.: 650,016

[22] Filed: Sep. 13, 1984

[30] Foreign Application Priority Data

Sep. 13, 1983 [DE] Fed. Rep. of Germany ....... 3332943

[51] Int. Cl.$^4$ ................................................. F25J 3/02
[52] U.S. Cl. .......................................... 62/18; 62/25; 62/29; 62/31; 62/34; 62/39
[58] Field of Search .................. 62/38, 39, 23, 24, 25, 62/29, 31, 34, 17, 18

[56] References Cited

U.S. PATENT DOCUMENTS 4,331,461 5/1982 Karbosky et al. ........................ 62/38

Primary Examiner—Frank Sever
Attorney, Agent, or Firm—Millen & White

[57] ABSTRACT

For the separation of ethane and higher hydrocarbons from a high pressure incoming gas containing hydrocarbons, the raw gas is cooled and expanded in several stages and the condensates that are produced are fed to a rectifying column to provide an overhead gaseous product essentially consisting of methane and a bottoms product consisting essentially of ethane and higher hydrocarbons. To save energy, the raw gas and/or the product streams are heat exchanged in parallel streams under different pressures, the cooled high-pressure gas is work-expanded and the condensates produced by cooling and expansion are fed separately to the rectifying column.

20 Claims, 3 Drawing Figures

PARALLEL STREAM HEAT EXCHANGE FOR SEPARATION OF ETHANE AND HIGHER HYDROCARBONS FROM A NATURAL OR REFINERY GAS

BACKGROUND OF THE INVENTION

This invention relates to a rectification system for the production of ethane and higher hydrocarbons from high pressure, hydrocarbon-containing feed gas in which the feed gas is cooled and expanded in several stages and the resulting condensates are fed to a rectifying column to provide an overhead product consisting essentially of methane and a bottom product consisting essentially of ethane and higher hydrocarbons.

There is a known process of treating natural gas or refinery gas, containing methane, ethane, propane and higher hydrocarbons, comprising the steps of freeing the gas of acid gases, such as $H_2S$ and $CO_2$, that are possibly present, and from water; cooling the resultant gas by external refrigeration and heat exchange with itself or fractions thereof in several cooling and phase separation stages; expanding the resulting condensates into a rectifying column at points that match the equilibrium compositions in the rectifying column; and work-expanding the gas phase of the last cooling stage in an expansion engine, e.g., a turbine. In the rectifying column, methane and small amounts of ethane are recovered as overhead gas at the top of the column, and a practically methane-free $C_{2+}$ fraction is obtained as the bottoms product. The gases resulting from the last expansion are recompressed and delivered as product gas (e.g., U.S. Pat. No. 4,061,481).

Frequently, the incoming gases are at various pressure levels. For example, crude oil mixed with gas is usually produced during the multistage expansion and subsequent stabilization of the crude oil. In this case, the gaseous fractions at various pressure levels have been brought to a single high pressure, dependent on the composition and purity of the products to be obtained, mostly around 60 to 70 bars, and then the further processing of the gaseous mixture is conducted at this pressure.

This known technique is extremely costly in energy. The fractions under low pressure contain mostly higher and thus heavier hydrocarbons, whose compression requires a considerable expenditure of energy. Moreover, in compression at high pressure, condensates result which contain water and possibly also acid gases and thus cannot be fed directly to fractionation.

SUMMARY

An object of this invention, therefore, is to provide a process and apparatus therefor of the type mentioned above that is more energy efficient.

A particular object is to provide such an improved process and apparatus for a system wherein the incoming gas is at a single pressure.

Another object is to provide such an improved process and apparatus for a system wherein the incoming gas comprises a plurality of streams at different pressures.

Upon further study of the specification and appended claims, further objects and advantages of this invention will become apparent to those skilled in the art.

To attain these objects, there is provided an improved process wherein the improvement comprises conducting parallel streams of incoming gas and/or product stream at different pressures through heat exchangers, work expanding resultant cooled high-pressure gas and feeding resultant condensates from the cooling and expansion stages separately to the rectifying column.

Thus, according to the invention, the incoming gas and/or product streams are processed in several pressure stages. The number of the pressure stages in this case is affected, among other things, by the composition of the gas, the amount of the respective fraction under a specific pressure, the final purity of the product fraction and the pretreatment of the gas, e.g., the preliminary cleaning of the gas. Two or three different pressure stages are preferably used; however, the invention is not limited to this number of pressure stages.

When, for example, two different pressure stages are used, for the most part, the fraction under the high pressure, which usually consists essentially of methane, ethane, small amounts of $C_{3+}$ hydrocarbons and water, is immediately further processed, while the remaining fractions, which are under lower pressure, are compressed to a medium pressure and then treated at this second pressure stage. In this way there is quickly obtained a preliminary separation of the gases, since the compositions of the gases to be processed at different pressure stages are already different.

In this connection, according to the invention, the expansion of the cooled high-pressure gas (fraction, which is under the highest pressure) is performed with an expander, e.g. a turbine. The liquid portion of the expanded fraction then serves as reflux for the rectifying column. Into the rectifying column the condensates resulting from the cooling are expanded separately and introduced at points corresponding to their equilibrium ratios and compositions. The low-pressure gases (fractions, which are under lower pressure) yield condensates that are relatively poor in methane, and at lower condensation temperatures effect an improved Q-T-rate, i.e. an improved possibility to cool down two or more feed gas streams in heat exchange with one or more cold product streams with low temperature differences.

The gas phase from the expander consists essentially of methane, which contains only small amounts of ethane. This gas can be mixed with the overhead product from the rectifying column without further processing.

The process of this invention has the great advantage of reducing the extent of which the raw incoming gas is to be compressed, thereby resulting in savings in both energy and equipment. Moreover, in conducting the process of the invention, the methane-burden on the rectifying column is lowered so that the column can be made smaller. Furthermore, better operational reliability is achieved by a reduction of equipment sizes. A still further advantage comprises the preliminary separation of the gases by separate processing.

Whereas it is clear from the present invention that more phase separators are needed, the fact that column can be made smaller due to the limited condensation of methane, more than offsets the cost of the additional phase separators.

According to another embodiment of the process according to the invention, the cooled high-pressure gas is expanded in the expander to a pressure above the pressure in the rectifying column. The resultant vapor portion from the engine expansion and the overhead product from the rectifying column are heated in parallel streams under different pressures. The high-pressure gas is expanded in the expander to a pressure clearly above the pressure of the rectifying column; for example, the pressure is 10 to 15 bars over that of the rectifying column. The particular pressure is dependent on the required $C_{2+}$ yield of the process, the higher the $C_{2+}$ yield, the more the gas must be expanded in the expander. The resulting condensate from the engine expansion is expanded in the rectifying column, while the vapor part is heated, not admixed with the overhead product of the column, but separately in parallel streams. Thus, two gaseous streams with different pressure levels are returned through the heat exchangers. The advantage of this process operation is in the saving of compression energy for recompression of the gas, since it is already in two pressure stages. Further, an improvement in the $C_{2+}$ yield is obtained.

Of course, this invention also contemplates an embodiment wherein the gas that is to be processed is under a single pressure, i.e. also when there is no cooling of different pressure streams conducted in parallel.

In a preferred process operation, the gases obtained at the respective lowest temperatures are heated at several pressure stages. The rectifying column is consequently fed only with condensates of the separators and can thereby operate at a lower pressure. The gases can be heated and recompressed either together or separately.

According to a particularly preferred embodiment of the invention, raw incoming gas is used to heat the rectifying column. After preliminary cleaning and drying, the gas streams, for example, under medium pressure, are partly cooled by being employed as reboiler heat for the rectifying column. This is possible since the rectifying column operates at lower pressures, and thus the boiling points of the hydrocarbons are also at lower temperatures. A temperature, which can easily be reached by heat exchange with the incoming gas at ambient temperature, is sufficient for rectifying the methane from the mixture in the column.

The process according to the invention can be used for all raw gases containing hydrocarbons, especially those obtained at different pressure levels, such as crude oil accompanied by gas.

BRIEF DESCRIPTION OF DRAWINGS

Preferred embodiments of the invention are illustrated schematically in the three figures, wherein.

DETAILED DESCRIPTION

Figure 1:
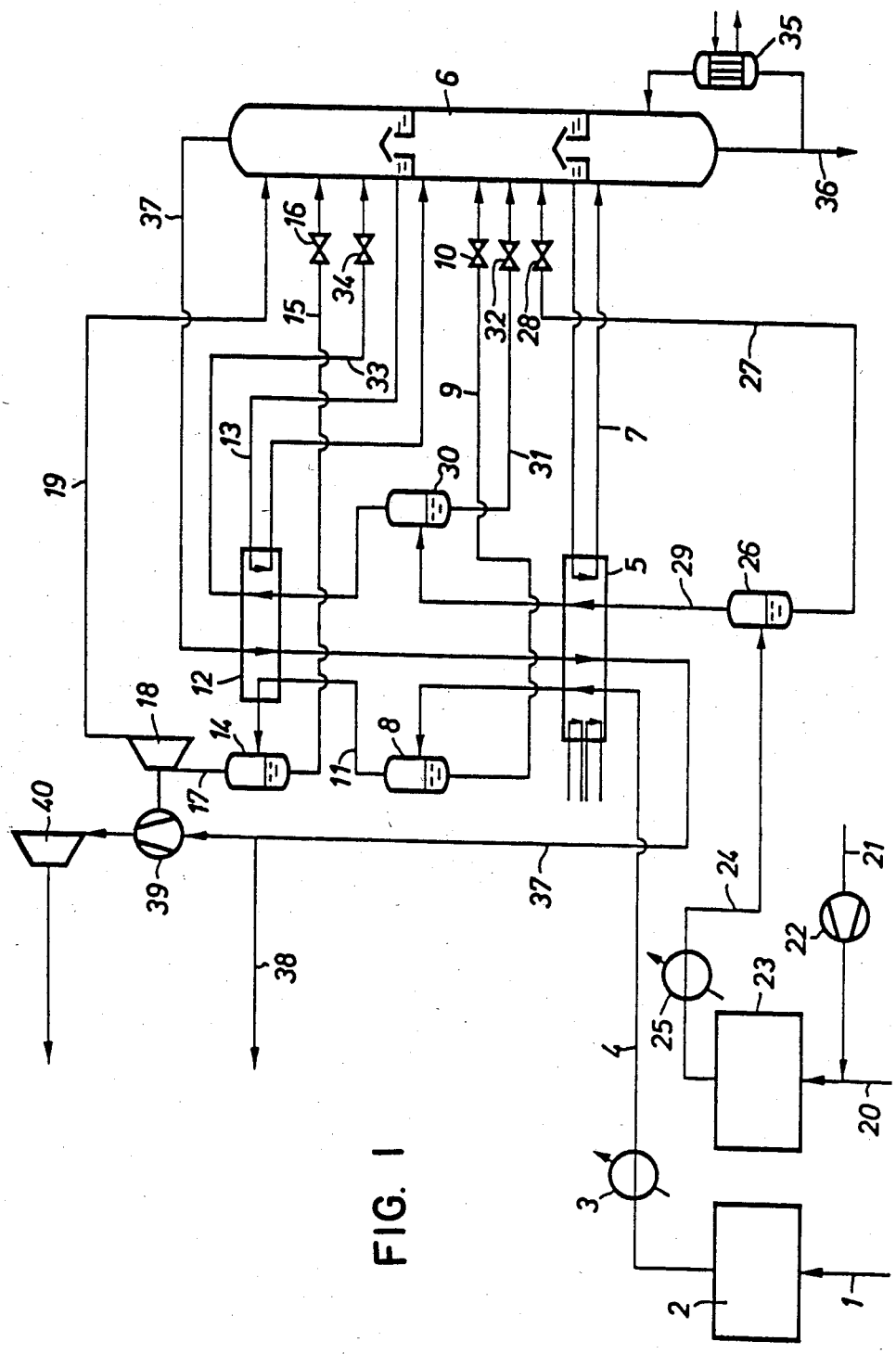
FIG. 1 shows a system with preliminary cooling in parallel streams starting with three starting gases at different pressures.

In the $C_{2+}$ separation plant according to FIG. 1, there is processed a crude-oil-derived gas under three different pressure stages. Pipe 1 feeds 614.3 mol/sec of a high-pressure gas (64 bars) at a temperature of 323 K. The gas has the following composition:

| | |
|---|---|
| $N_2$ | 1.86 mol % |
| $CH_4$ | 84.46 mol % |
| $C_2H_6$ | 9.24 mol % |
| $C_{3+}$ | 4.36 mol % |

-continued

| | |
|---|---|
| $H_2O$ | 0.08 mol %. |

The gas, resulting from an upstream acid gas removal stage and saturated with water, is treated in an adsorber 2, e.g., a special molecular sieve for the drying of natural gases of similarly gases provided by many companies, e.g., UCC, Grace, Bayer AG, to remove $H_2O$ to prevent ice formation in the subsequent low temperature stage. Substantially only water is removed from the gas stream in adsorber 2; i.e. coadsorption of the hydrocarbons is reduced to a minimum. In this connection, two adsorbers are normally used, which are alternately loaded and regenerated. The adsorber is regenerated at conventional elevated temperature for the desorption of $H_2O$. After desorption, the adsorber is re-cooled to the operating temperature of 323 K.

The dried gas (613.8 mol/sec) leaving adsorber 2 by pipe 4, is cooled first by external refrigeration (e.g., $C_3$ refrigeration) in a cooler 3 to 293 K. and then to 237 K. in a first heat exchanger 5 cooled by external refrigeration, cold overhead products from a rectifying column 6 (which will be discussed more in detail below) and a cold liquid stream partially reboiled from the side of the rectifying column. The resultant cooled fluid is fed to phase separator 8. The condensate stream (49.3 mol/sec) from separator 8 is fed into rectifying column 6 by pipe 9 via pressure reduction valve 10. The vapor fraction (564.5 mol/sec) from phase separator 8 is fed by pipe 11 to a second heat exchanger 12, cooled there by the cold overhead product from rectifying column 6 and by a second side reboiler stream 13 to 224 K. and fed to a phase separator 14. A condensate stream (33.7 mol/sec) is withdrawn from the phase separator via conduit 15 and expanded via valve 16 into the rectifying column 6. The gas phase (530.8 mol/sec) withdrawn from separator 14 by a pipe 17 is expanded via turboexpander 18 and is fed via conduit 19 in gaseous and a liquid state to the top of rectifying column 6. The liquid part of this stream is used as reflux within the rectifying column.

Two other raw gas streams are fed to the $C_{2+}$ separation installation; they come from two other expansion stages and stabilization stages of the crude oil treatment process and therefore are under lower pressure than the first gas and contain a higher portion of heavier hydrocarbons. A gas under a medium pressure of 34 bars is introduced by pipe 20 and a gas under low pressure of 15 bars is fed in by pipe 21. The low-pressure gas in 21 is compressed in a compressor 22 to 34 bars and, with the medium-pressure gas, is fed to an adsorber 23. The gas (385.7 mol/sec) is at a temperature of 323 K. and has the following composition:

| | |
|---|---|
| $N_2$ | 0.39 mol % |
| $CH_4$ | 48.24 mol % |
| $C_2H_6$ | 21.62 mol % |
| $C_{3+}$ | 29.39 mol % |
| $H_2O$ | 0.36 mol % |

This gas can also come from an upstream acid gas separation stage, installed in the circuit, and is saturated with water. This gas must also be dried to prevent ice formation in the subsequent low temperature stage. The gas therefore is freed of water in adsorber 23 in the same way as the high-pressure gas. Then 384.3 mol/sec of the dried gas, conveyed in pipe 24, is cooled to 293 K. in an externally refrigerated cooler 25 (e.g., $C_3$ refrigeration) and fed to a phase separator 26. From phase separator 26, 88.6 mol/sec of condensate are passed via conduit 27 and expanded via valve 28 into rectifying column 6. From separator 26, 295.7 mol/sec of vapor gas are withdrawn in conduit 29, cooled to 237 K. in heat exchanger 5, and the resultant fluid is introduced into phase separator 30. From phase separator 30, 126.0 mol/sec of condensate are expanded into rectifying column 6 via pipe 31 and valve 32, while the vapor (169.7 mol/sec) from separator 30 is cooled in heat exchanger 12 to 200 K. and is expanded by pipe 33 via valve 34 into rectifying column 6. The fluids expanded into the rectifying column via valves 28, 32 and 16 are approximately about 95% liquid, 95% liquid and 58% liquid, respectively, (based on the mol/sec of the expanded liquid).

All the described condensates or gases are fed into the rectifying column 6 at points in the column where the respective compositions match.

The rectifying column, operated under a pressure of 28 bars, is operated in a temperature range between 193 K. at the top and 315 K. at the bottom. The bottom of the column is heated by a reboiler 35 externally heated by a thermal fluid, e.g. low pressure steam, hot water or warm feedgas. The practically-methane free $C_{2+}$ fraction collects at the bottom of the column and is removed by pipe 36. This fraction is produced in an amount of 251.5 mol/sec with a temperature of 315 K. and has the following composition:

| $CH_4$ | 1.0 mol % |
|---|---|
| $C_2H_6$ | 43.86 mol % |
| $C_{3+}$ | 55.14 mol %. |

The $C_{2+}$ fraction can be subjected to an additional separation in subsequent process steps.

746.6 Mol/sec of product gas with the composition:

| $N_2$ | 1.72 mol % |
|---|---|
| $CH_4$ | 94.07 mol % |
| $C_2H_6$ | 4.0 mol % |
| $C_{3+}$ | 0.21 mol % | are removed as overhead gas from the top of rectifying column 6 by pipe 37. This product gas has a temperature of 193 K. and is heated in heat exchangers 12 and 5 to 290 K. and in part (71.6 mol/sec) is fed under a pressure of 27 bars by pipe 38 for use as regenerating gas for the adsorber (heating by high pressure steam is not shown) and as fuel gas for the whole plant, and in part (675.0 mol/sec) is compressed in compressors 39 and 40 to 56 bars, cooled in a subsequent air cooler, not shown, to 323 K. and delivered for consumption. It is seen that compressor 39 is preferably coupled to turboexpander 18, but whether such a mechanical or electrical coupling is employed in a given facility will depend on a cost analysis of all pertinent factors.

Figure 2:
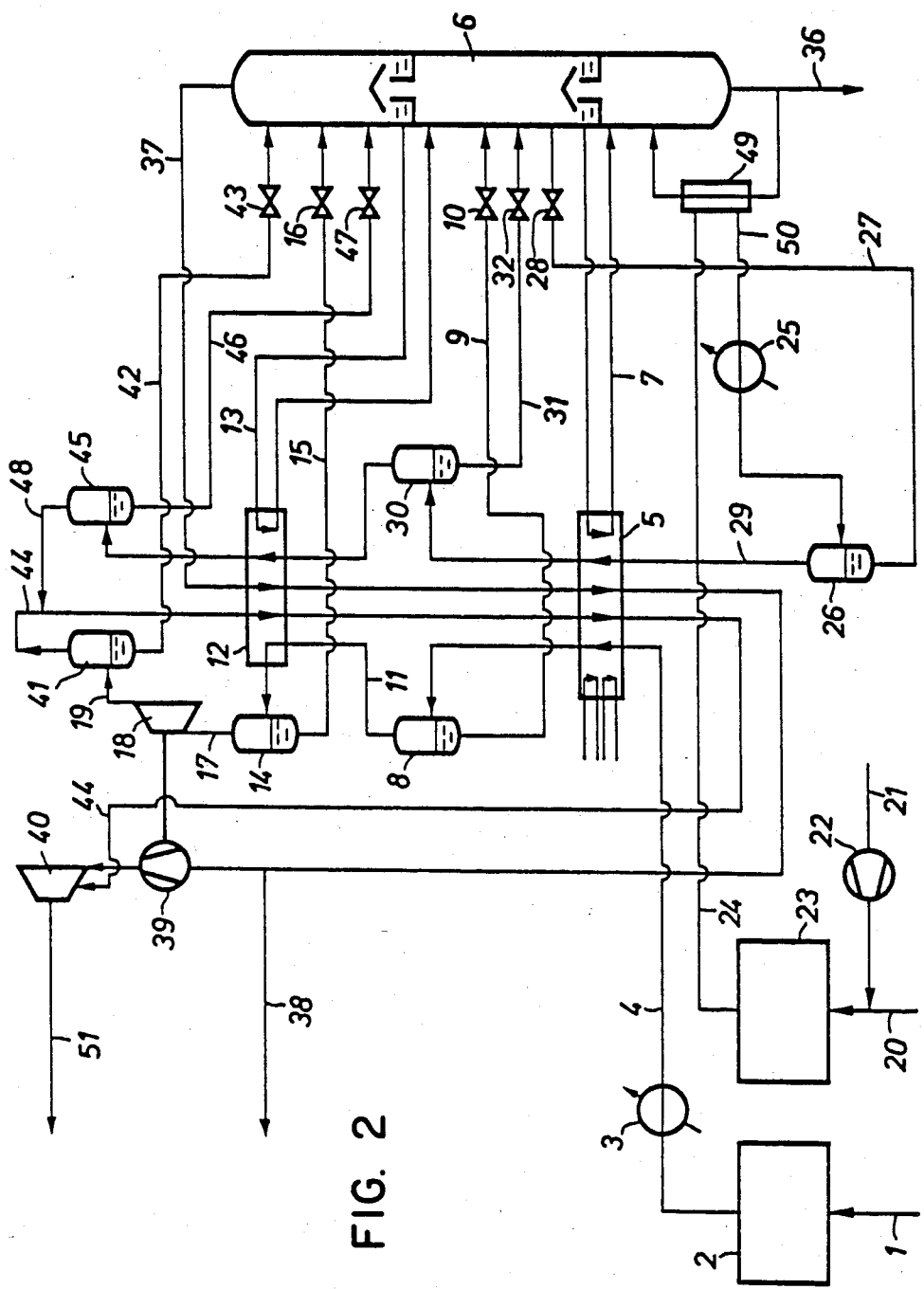
FIG. 2 shows a system with parallel preliminary cooling streams as in FIG. 1 and also and in return different pressure parallel streams through the precoolers.

In the embodiment according to FIG. 2, the same plant sections are given the same reference numbers as in FIG. 1. The same pressure, the same gas composition, amount and temperature have been selected for direct comparison of the two embodiments. Normally, according to this embodiment, the pressure of the medium-pressure gas can be reduced and thereby, compression energy can be saved.

Some essential differences, inter alia, from the embodiment according to FIG. 1, are that a vapor phase from the turbine 18 is not fed to the rectifying column 6, the reboiling of the bottoms of the rectifying column is conducted with the medium-pressure gas process, a fraction of the product gas is produced by fractional condensation rather than rectification, and the product gas is recycled through the precoolers at two different pressures.

The gas from separator 14 is work-expanded in turbine 18 to a pressure that is substantially above the pressure in the rectifying column, for example, in the present case, to 28 bars in case of a pressure of 17 bars in the rectifying column. The gas with a temperature of 194 K. is then fed to a phase separator 41 by a pipe 19. The condensate from phase separator 41 is expanded into rectifying column 6 via pipe 42 through valve 43 with a temperature of 181 K. On the other hand, the gas from separator 41 is recycled by pipe 44 and heated in heat exchangers 12 and 5 to 290 K. Also different is that after heat exchanger 12, the gas from phase separator 30 is fed to another phase separator 45. The condensate from this separator 45 is expanded into rectifying column 6 via pipe 46 through valve 47. The gas withdrawn from phase separator 45, at a temperature of 197 K., is mixed via pipe 48 with the gas from separator 41 in pipe 44 and heated with it. Thus, 573.3 mol/sec of a "high-pressure product gas" with the following composition are produced under a pressure of 28.6 bars:

| $N_2$ | 2.08 mol % |
|---|---|
| $CH_4$ | 93.64 mol % |
| $C_2H_6$ | 4.07 mol % |
| $C_{3+}$ | 0.21 mol % |

Rectifying column 6 is operated at a pressure of 17 bars, as a result of which the boiling point of the bottoms product is at a lower temperature than in embodiment 1. The rectifying column is therefore operated in a temperature range of 181 K. at the top and 286 K. at the bottom. In this case, this relatively low bottom temperature can be produced by indirect heat exchange by the gas under medium pressure. For this purpose, the dried medium pressure gas is fed from pipe 24 to a heat exchanger 49 and is cooled in heat exchange with a partial stream of the bottom product. The preliminarily cooled medium pressure gas is then fed by pipe 50 to cooler 25 and processed as described in FIG. 1.

252.8 Mol/sec of $C_{2+}$ hydrocarbons with a temperature of 286 K. and the following composition are removed from the bottom of column 6 by pipe 36 and optionally fed to another separation:

| $CH_4$ | 1.00 mol % |
|---|---|
| $C_2H_6$ | 44.08 mol % |
| $C_{3+}$ | 54.92 mol % |

172.0 Mol/sec of product gas with a temperature of 181 K. are removed as overhead gas from the top of rectifying column 6 by pipe 37 and heated in heat exchangers 12 and 5 to 290 K. The product gas has the following composition:

| $N_2$ | 0.55 mol % |
|---|---|
| $CH_4$ | 96.21 mol % |
| $C_2H_6$ | 3.13 mol % |

-continued

| | |
|---|---|
| $C_{3+}$ | 0.11 mol % |

A part (71.6 mol/sec) of the product gas under a pressure of 16.6 bars in conduit 38 is used as regenerating gas for the adsorber in the same manner as FIG. 1, while the other part (100.4 mol/sec) is compressed in compressors 39 and 40, cooled in a subsequent air cooler, not shown, to 323 K. and fed to the delivery network by pipe 51.

The consumption figures of the two embodiments acording to the invention in comparison with the state of the art are indicated in the following table. As the state of the art a process is taken in which the fractions used, which are at different pressure levels, are all condensed at high pressure, with further processing being otherwise the same. Initially, conditions were the same in all cases, i.e. a raw gas pressure of 64 bars and 34 bars respectively, a total amount of gas of 1000 mol/sec, a product gas compression to 56 bars with a fuel gas rate of 71.6 mol/sec. In all cases the $C_{2+}$ yield was 78%. The fluids expanded into the rectifying column via valves 28, 32 and 16 are approximately about 83% liquid, 82% liquid and 48% liquid, respectively, based on the mol/sec of the expanded liquid.

TABLE
Electrical Energy Consumption Figures of the Embodiments According to the Invention in Comparison with the State of the Art

| | | Total Compression | Refrigerating Compressor | Total Electrical Energy Requirement |
|---|---|---|---|---|
| State of the art. | Raw gas Product gas | 1.66 MW | 2.06 MW | 3.72 MW |
| 2 pressure stages in the precooling stages. | Raw gas Product gas | 1.26 MW | 1.94 MW | 3.20 MW |
| 2 pressure stages in precooling stages and 2 pressure stages in the return of cold product gas through the precoolers | Raw gas Product gas | 1.38 MW | 1.47 MW | 2.85 |

External refrigeration is used for the precooling of the feed gas streams to 293 K. in 3 and 25 and in the heat exchanger 5.

Figure 3:
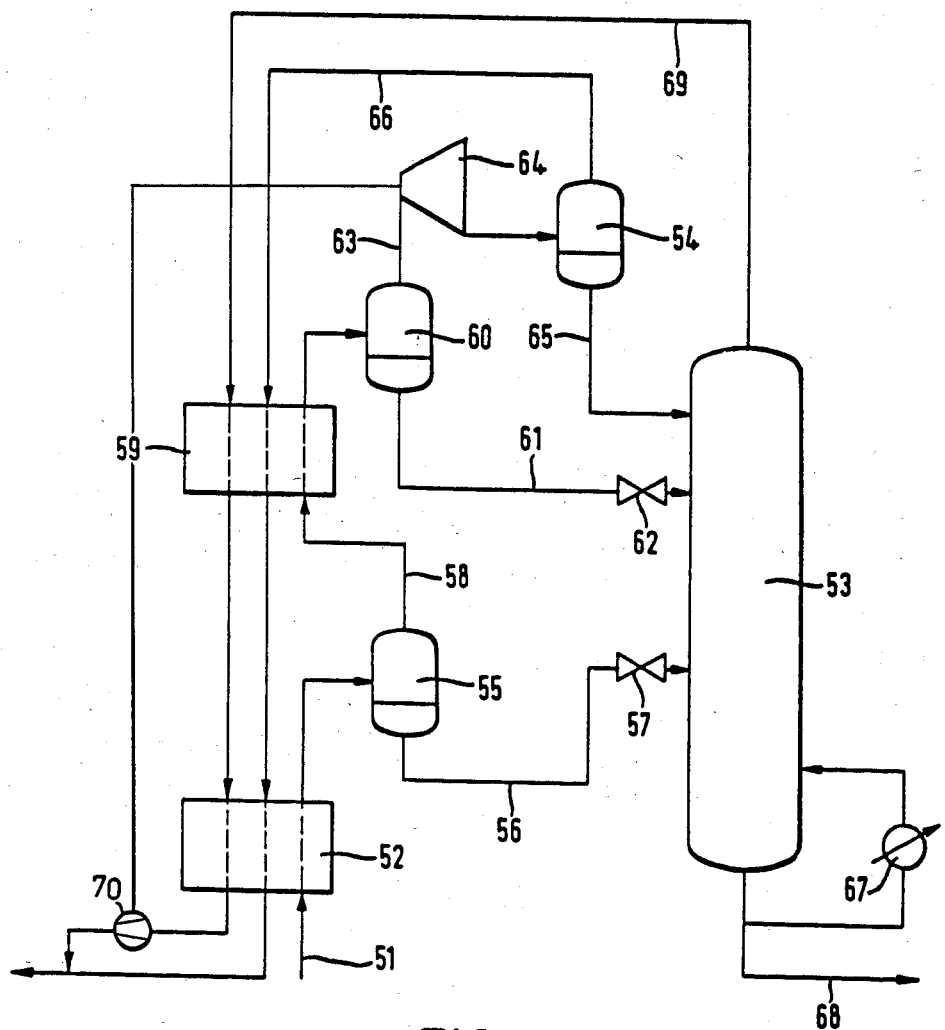
FIG. 3 shows a system with parallel return streams but with a starting gas of single pressure.

Referring now to FIG. 3, there is shown the production of $C_{2+}$ hydrocarbons, for example, from a crude oil mixed with a gas under a single pressure by the use of two pressure stages in the return of the gases through the preliminary coolers.

1000 Mol/sec of a gas under a pressure of 56 bars and a temperature of 293 K. is fed by pipe 51. The gas exhibits the following composition:

| | |
|---|---|
| $CH_4$ | 84.78 mol % |
| $C_2H_6$ | 11.96 mol % |
| $C_3H_8$ | 3.26 mol % |

The gas can be obtained from an upstream acid gas removal stage installed in the circuit and, for example, an adsorptive drying stage.

The gas is cooled in a first heat exchanger 52 by the cold overhead product of a rectifying column 53 and a phase separator 54, which will be discussed in detail below, to 234 K. and fed to a phase separator 55. A first condensate stream (45 mol/sec) is expanded into rectifying column 53 via pipe 56 through valve 57, while the vapor fraction (955 mol/sec) is fed to a second heat exchanger 59 via pipe 58. There, this fraction is also cooled by the cold overhead product of rectifying column 53 and phase separator 54 to 214.7 K. and fed to a phase separator 60. From this phase separator, a second condensate stream (346 mol/sec) is expanded into rectifying column 53 via pipe 61 through valve 62. The gas (609 mol/sec) is fed to an expansion engine, e.g. a turbine 64 by pipe 63, expanded and fed at 182 K. to phase separator 54. The condensate (106 mol/sec) from separator 54 is fed to the upper part of the rectifying column by pipe 65 via expansion valve (not shown). Conversely, the gas from the phase separator is returned at a pressure of 22.5 bars by pipe 66, and heated in heat exchangers 59 and 52 to 289 K. The fluids expanded into the rectifying column via valves 57, 62, and in conduit 65 are approximately about 55% liquid, 46% liquid and 86% liquid, respectively, based on the mol/sec of the expanded liquid.

Rectifying column 53 is operated under a pressure of 16 bars and at a temperature range between 173 K. at the top and 265 K. at the bottom. The bottom of the column is heated by a reboiler 67. The practically methane-free $C_{2+}$ fraction accumulates at the bottom of the column and is removed by pipe 68. This fraction is produced at a rate of 131.6 mol/sec, at a temperature of 265 K. and under a pressure of 16 bars, and has the following composition:

| | |
|---|---|
| $CH_4$ | 0.70 mol % |
| $C_2H_6$ | 74.66 mol % |
| $C_3H_8$ | 24.64 mol % |

At the top of the rectifying column 360 mol/sec of product gas with the following composition is removed by pipe 69.

| | |
|---|---|
| $CH_4$ | 97.7 mol % |
| $C_2H_6$ | 2.19 mol % |
| $C_3H_8$ | 0.03 mol % |

The product gas has a temperature of 173 K. and a pressure of 16 bars. Thereafter it is heated in heat exchangers 59 and 52 to 289 K. and delivered with the gas from pipe 66 as sales gas.

The gas from column 53 is compressed to 22 bars in a separate compressor 70 after being warmed up, and then it is compressed together with the gas from separator 54 (conduit 66) to the delivery pressure of the sales gas.

The electric power demand for production of the external refrigeration amounts of 0.72 MW in the process according to FIG. 3, while in a process according to the state of the art 1.27 MW must be used. A process in which the product is delivered under a single pressure (column pressure) is taken as the state of the art.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. In a process for the separation of ethane and higher hydrocarbons from incoming raw gas under pressure containing methane, ethane and higher hydrocarbons, comprising cooling and expanding said incoming gas in several serially connected stages comprising heat exchangers and phase separators and withdrawing resulting condensates from the corresponding phase separators of each stage, work expanding resultant cooling high-pressure gas from a phase separator and feeding resultant condensates from the cooling and expansion stages to a rectifying column, and withdrawing from said rectifying column an overhead gaseous product consisting essentially of methane and a bottoms product consisting essentially of ethane and higher hydrocarbons, the improvement comprising, passing the incoming gas into the process in at least two separate streams, said streams being under different pressures, and conducting said cooling of said different streams of incoming gas in parallel in at least one of the same heat exchangers, and in indirect heat exchange with said overhead gaseous product consisting essentially of methane.

2. A process according to claim 1, wherein the resultant cooled high-pressure gas is work-expanded to a pressure above the operating pressure of the rectifying column; the resultant work-expanded fluid is separated into vapor and liquid phases; and the vapor phase and the overhead product of the rectifying column are at different pressures and are passed in parallel streams through said heat exchangers where they are heated while cooling said incoming gas.

3. A process according to claim 2, wherein incoming gas is employed in indirect heat exchange relationship as reboiler heat for said rectifying column.

4. A process according to claim 3, wherein resultant heated product gases are compressed, at least in part, to a pressure higher than the operating pressure of the rectifying column.

5. A process according to claim 2, wherein resultant heated product gases are compressed, at least in part, to a pressure higher than the operating pressure of the rectifying column.

6. A process according to claim 1, wherein said incoming streams are under three different pressures, and the lowest pressure stream is compressed to the pressure of the intermediate pressure stream and admixed therewith prior to cooling said stream.

7. A process according to claim 6, wherein the resultant cooled high-pressure gas is work-expanded to a pressure above the operating pressure of the rectifying column; the resultant work-expanded fluid is separated into vapor and liquid phases; and the vapor phase and the overhead product of the rectifying column are at different pressures and are passed in parallel streams through said heat exchangers where they are heated while cooling said incoming gas.

8. A process according to claim 7, wherein incoming gas is employed in indirect heat exchange relationship as reboiler heat for said rectifying column.

9. A process according to claim 6, wherein incoming gas is employed in indirect heat exchange relationship as reboiler heat for said rectifying column.

10. A process according to claim 1, wherein said incoming streams are cooled in parallel in at least two of the same heat exchangers.

11. A process according to claim 10, wherein incoming gas is employed in indirect heat exchange relationship as reboiler heat for said rectifying column.

12. A process according to claim 1, wherein incoming gas is employed in indirect heat exchange relationship as reboiler heat for said rectifying column.

13. In a process for the separation of ethane and higher hydrocarbons from incoming raw gas under pressure containing methane, ethane and higher hydrocarbons, comprising cooling and expanding said incoming gas in several serially connected stages comprising heat exchangers and phase separators and withdrawing resulting condensates from the corresponding phase separators of each stage, work expanding resultant cooling high-pressure gas from a phase separator and feeding resultant condensates from the cooling and expansion stages to a rectifying column, and withdrawing from said rectifying column an overhead gaseous product consisting essentially of methane and a bottoms product consisting essentially of ethane and higher hydrocarbons, the improvement comprising, work expanding the resultant cooled high-pressure gas to a pressure above the operating pressure of the rectifying column; separating the resultant work-expanded fluid into vapor and liquid phases; passing and the resultant vapor phase and said overhead product from the rectifying column, under different pressures, in parallel streams through at least one of said heat exchangers where said resultant vapor phase and said overhead gaseous product are heated while cooling said incoming gas.

14. A process according to claim 13, wherein the incoming gas enters the process in at least two separate streams, said streams being under different pressures.

15. A process according to claim 14, wherein incoming gas is employed in indirect heat exchange relationship as reboiler heat for said rectifying column.

16. A process according to claim 14, wherein resultant heated product gases are compressed, at least in part, to a pressure higher than the operating pressure of the rectifying column.

17. A process according to claim 16, wherein the incoming gas is employed in indirect heat exchange relationship as reboiler heat for said rectifying column.

18. A process according to claim 13, wherein the incoming gas is under a single pressure.

19. A process according to claim 18, wherein resultant heated product gases are compressed, at least in part, to a pressure higher than the operating pressure of the rectifying column.

20. A process according to claim 13, wherein resultant heated product gases are compressed, at least in part, to a pressure higher than the operating pressure of the rectifying column.

* * * * *